(12) United States Patent
Chen (10) Patent No.: US 10,431,626 B2
(45) Date of Patent: Oct. 1, 2019

(54) IMAGE SENSOR DEVICES

(71) Applicant: Silicon Optronics, Inc., Hsinchu (TW)

(72) Inventor: Jun-Bo Chen, Hsinchu (TW)

(73) Assignee: Silicon Optronics, Inc., Hsinchu (TW)

( * ) Notice: Subject to any disclaimer, the term of this patent is extended or adjusted under 35 U.S.C. 154(b) by 0 days.

(21) Appl. No.: 15/876,704

(22) Filed: Jan. 22, 2018

(65) Prior Publication Data

US 2019/0181164 A1   Jun. 13, 2019

(30) Foreign Application Priority Data

Dec. 7, 2017   (TW) .............................. 106142915 A (51) Int. Cl.
*H01L 27/14* (2006.01)
*H01L 27/30* (2006.01)
(Continued)

(52) U.S. Cl.
CPC ........ *H01L 27/148* (2013.01); *H01L 27/1464* (2013.01); *H01L 27/14643* (2013.01); *A61B 5/7203* (2013.01); *H01L 27/1462* (2013.01); *H01L 27/14603* (2013.01); *H01L 27/14623* (2013.01); *H01L 27/14625* (2013.01); *H01L 27/14627* (2013.01); *H01L 27/14636* (2013.01); *H01L 27/14678* (2013.01); *H01L 27/14683* (2013.01); *H01L 27/307* (2013.01); *H03M 2201/8192* (2013.01)

(58) Field of Classification Search
CPC ......... H01L 27/14623; H01L 27/14627; H01L 27/14678; H01L 27/148; H01L 27/1464; H01L 27/14643; H01L 27/1462; H01L 27/14636; H01L 27/307; H03M 2201/8192

See application file for complete search history.

(56) References Cited

U.S. PATENT DOCUMENTS 7,446,359 B2 *  11/2008  Lee .................... H01L 27/14603
                                                        257/291
7,655,495 B2 *   2/2010  Adkisson .......... H01L 21/76819
                                                        438/144
(Continued)

FOREIGN PATENT DOCUMENTS

TW         200414281 A     8/2004
TW         201332092 A1    8/2013
TW         201715716 A     5/2017

*Primary Examiner* — Ida M Soward
(74) *Attorney, Agent, or Firm* — Muncy, Geissler, Olds & Lowe, P.C.

(57) ABSTRACT

An image sensor device is provided. The image sensor device includes a substrate, a plurality of photoelectric conversion units for collecting image signals disposed in the substrate, a first dielectric layer disposed upon the substrate, a plurality of metal layers disposed in the first dielectric layer, a trench disposed in the first dielectric layer and located between the adjacent metal layers, a filling material filled in the trench, a second dielectric layer disposed upon the first dielectric layer, and a light source or a detected object disposed over the second dielectric layer. The metal layer adjacent to the substrate is defined as a first metal layer. The metal layer adjacent to the top of the first dielectric layer is defined as a top metal layer. The trench extends from the top of the first dielectric layer towards the substrate to the first metal layer.

17 Claims, 4 Drawing Sheets

(51) Int. Cl.
  *H01L 27/148*  (2006.01)
  *H01L 27/146*  (2006.01)
  *A61B 5/00*    (2006.01)

(56) References Cited

U.S. PATENT DOCUMENTS

| | | | | |
|---|---|---|---|---|
| 7,714,535 | B2* | 5/2010 | Yamazaki | H01Q 1/36 |
| | | | | 320/107 |
| 7,759,712 | B2* | 7/2010 | Yamamura | H01L 27/1462 |
| | | | | 257/292 |
| 8,198,693 | B2* | 6/2012 | Mizuno | H01L 27/14627 |
| | | | | 257/432 |
| 8,427,563 | B2* | 4/2013 | Kim | H01L 27/14621 |
| | | | | 348/273 |
| 9,231,016 | B2* | 1/2016 | Horikoshi | H01L 27/14625 |
| 9,391,112 | B2* | 7/2016 | Shimotsusa | H01L 21/76898 |
| 9,601,533 | B2* | 3/2017 | Tsukagoshi | H01L 27/14625 |
| 9,871,148 | B2* | 1/2018 | Mizuta | H01L 27/14623 |
| 9,941,321 | B2* | 4/2018 | Matsugai | H01L 22/12 |
| 2007/0001252 | A1* | 1/2007 | Noda | H01L 27/14621 |
| | | | | 257/432 |
| 2008/0105908 | A1* | 5/2008 | Lee | H01L 27/14623 |
| | | | | 257/290 |
| 2009/0065820 | A1* | 3/2009 | Kao | H01L 27/14632 |
| | | | | 257/292 |
| 2010/0103288 | A1* | 4/2010 | Ahn | H01L 27/14621 |
| | | | | 348/231.99 |
| 2010/0204064 | A1 | 8/2010 | Cho | |
| 2011/0242376 | A1 | 10/2011 | Ando | |
| 2013/0249038 | A1* | 9/2013 | Tay | H01L 27/14603 |
| | | | | 257/432 |
| 2013/0267058 | A1* | 10/2013 | Lee | H01L 27/14609 |
| | | | | 438/72 |
| 2013/0285131 | A1* | 10/2013 | Matsumoto | H01L 27/14609 |
| | | | | 257/291 |
| 2015/0349015 | A1* | 12/2015 | Yamaguchi | H01L 27/14645 |
| | | | | 257/432 |
| 2018/0122852 | A1* | 5/2018 | Nishimura | H01L 27/14843 |
| 2018/0155782 | A1* | 6/2018 | Zhong | G01N 21/645 |

* cited by examiner

IMAGE SENSOR DEVICES

CROSS REFERENCE TO RELATED APPLICATIONS

This Application claims priority of Taiwan Patent Application No. 106142915, filed on Dec. 7, 2017, the entirety of which is incorporated by reference herein.

TECHNICAL FIELD

The technical field relates to an image sensor device capable of effectively collecting optical signals and improving signal-to-noise ratio (SNR), especially for biomedical sensing applications.

BACKGROUND

An image sensor device is a kind of semiconductor device that transforms optical images into electrical signals. Image sensor devices can generally be classified into two groups: charge coupled device (CCD) image sensor devices and complementary metal oxide semiconductor (CMOS) image sensor devices. Among these image sensor devices, the CMOS image sensor device comprises a photodiode for detecting incident light and transforming it into electrical signals, and logic circuits for transmitting and processing the electrical signals.

Among current image sensor devices, in addition to the traditional applications for sensing images, more and more image sensor devices have been applied to various types of detection tasks, for example, biomedical detection, and using an external light source to irradiate a detected object to emit an excitation light to detect or determine the characteristics of the detected object.

However, whether it is being used for sensing images or for performing various other detection tasks, the image sensor device still suffers from some thorny problems, such as the cross-talk phenomenon and low signal-to-noise ratio (SNR), which can affect the device's performance.

Therefore, development of an improved image sensor device which is capable of effectively collecting optical signals and improving signal-to-noise ratio (SNR) is desirable.

SUMMARY

In accordance with one embodiment of the invention, an image sensor device is provided. The image sensor device comprises a substrate, a plurality of photoelectric conversion units for collecting image signals disposed in the substrate, a first dielectric layer disposed upon the substrate, a plurality of metal layers disposed in the first dielectric layer, a trench disposed in the first dielectric layer and located between the adjacent metal layers, a filling material filled in the trench, a second dielectric layer disposed upon the first dielectric layer, and a light source or a detected object disposed over the second dielectric layer. The metal layer adjacent to the substrate is defined as a first metal layer. The metal layer adjacent to the top of the first dielectric layer is defined as a top metal layer. The trench is an optical path to collect optical signals. The trench extends from the top of the first dielectric layer towards the substrate to the first metal layer. The filling material is a high-refractive-index material, or a material which allows or blocks light with specific wavelengths to pass through.

In accordance with some embodiments of the invention, the first dielectric layer is an oxide layer.

In accordance with some embodiments of the invention, the filling material is a material which has a refractive index higher than 1.4 or a material which allows or blocks light with specific wavelengths to pass through, or a material which blocks light with specific wavelengths.

In accordance with some embodiments of the invention, the high-refractive-index material is a material which has a refractive index of 1.8-2.2, or a material blocking green light.

In accordance with some embodiments of the invention, the second dielectric layer is a silicon nitride layer or other suitable materials.

In accordance with some embodiments of the invention, the trench is in contact with the top metal layer, and there is no gap therebetween.

In accordance with some embodiments of the invention, the image sensor device further comprises a light-shielding layer disposed at the top of the first dielectric layer.

In accordance with some embodiments of the invention, the light-shielding layer comprises metals, light-blocking materials, or light-absorbing materials.

In accordance with some embodiments of the invention, the trench is in contact with the light-shielding layer, and there is no gap therebetween.

In accordance with some embodiments of the invention, the detected object is biomolecules.

In accordance with one embodiment of the invention, an image sensor device is provided. The image sensor device comprises a substrate, a plurality of photoelectric conversion units for collecting image signals disposed in the substrate, a first dielectric layer disposed upon the substrate, a light-shielding layer disposed at the top of the first dielectric layer, a trench disposed in the first dielectric layer, a filling material filled in the trench, a second dielectric layer disposed upon the first dielectric layer, and a light source or a detected object disposed over the second dielectric layer. The trench is an optical path to collect optical signals. The trench extends from the top of the first dielectric layer to the substrate and is in contact with the light-shielding layer. In addition, the filling material is a high-refractive-index material, or a material which allows or blocks light with specific wavelengths to pass through.

A detailed description is given in the following embodiments with reference to the accompanying drawings.

BRIEF DESCRIPTION OF THE DRAWINGS

The invention can be more fully understood by reading the subsequent detailed descriptions and examples with references made to the accompanying drawings, wherein.

DETAILED DESCRIPTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
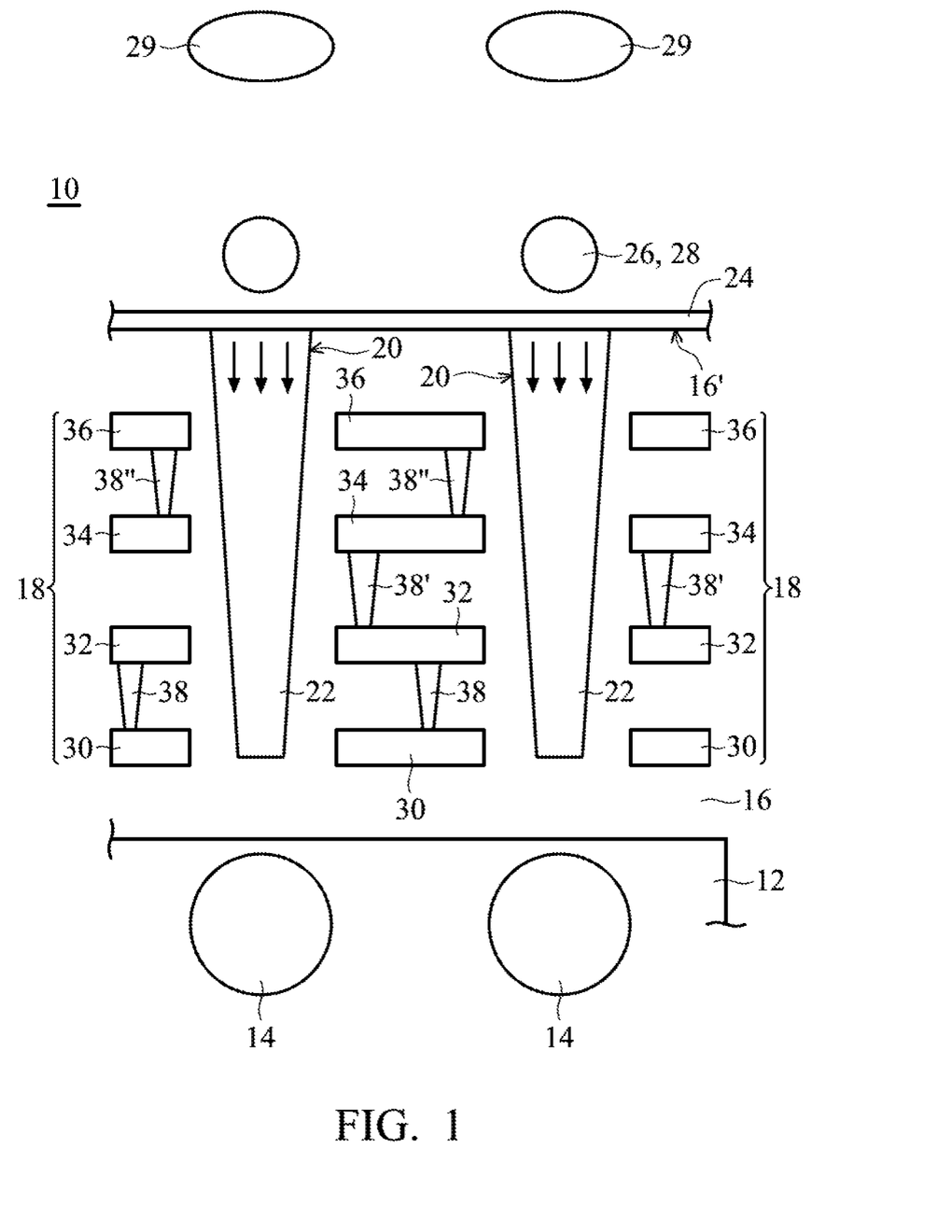
FIG. 1 is a cross-sectional view of an image sensor device in accordance with one embodiment of the invention.

Referring to FIG. 1, in accordance with one embodiment of the invention, an image sensor device 10 is disclosed. FIG. 1 is a cross-sectional view of the image sensor device 10 in this embodiment.

As shown in FIG. 1, the image sensor device 10 comprises a substrate 12, a plurality of photoelectric conversion units 14 for collecting image signals, a first dielectric layer 16, a plurality of metal layers 18, a trench 20, a filling material 22, a second dielectric layer 24 and a light source 26.

In this embodiment, the image sensor device 10 is a front side illumination (FSI) image sensor device.

In accordance with some embodiments of the invention, the image sensor device 10 may also comprise a detected object 28 and a detection light source 29.

As shown in FIG. 1, the photoelectric conversion units 14 are disposed in the substrate 12. The first dielectric layer 16 is disposed upon the substrate 12. The metal layers 18 are disposed in the first dielectric layer 16.

In this embodiment, the metal layers 18 comprise a first metal layer 30, a second metal layer 32, a third metal layer 34 and a top metal layer 36. The first metal layer 30 is adjacent to the substrate 12. The top metal layer 36 is adjacent to the top 16' of the first dielectric layer 16. Electrical connections are formed between individual metal layers by plugs (38, 38' and 38") in the metal layers 18. For example, an electrical connection is formed between the first metal layer 30 and the second metal layer 32 by a first plug 38. An electrical connection is formed between the second metal layer 32 and the third metal layer 34 by a second plug 38'. An electrical connection is formed between the third metal layer 34 and the top metal layer 36 by a third plug 38".

The trench 20 is disposed in the first dielectric layer 16 and located between the adjacent metal layers. For example, the trench 20 is located between the adjacent first metal layers 30, located between the adjacent second metal layers 32, located between the adjacent third metal layers 34, and located between the adjacent top metal layers 36. The trench 20 extends from the top 16' of the first dielectric layer 16 towards the substrate 12 to the first metal layer 30.

In this embodiment, the depth of the trench 20 extending towards the substrate 12 does not extend past the first metal layer 30. However, if the product is acceptable for the characteristics of high dark current, the trench 20 may also extend to the substrate 12.

The filling material 22 filled in the trench 20 may comprise a high-refractive-index material, or a material which allows light with specific wavelengths to pass through, or a material which blocks light with specific wavelengths, to form a light guide element between the light source 26 or the detected object 28 and the photoelectric conversion units 14. The filling material 22 may also comprise other suitable materials, for example, a material that has a higher refractive index than that of the adjacent dielectric layer.

The second dielectric layer 24 is disposed upon the first dielectric layer 16. The light source 26 is disposed over the second dielectric layer 24.

In accordance with some embodiments of the invention, the detected object 28 may also be disposed over the second dielectric layer 24. The detected object 28 may be located over the second dielectric layer 24 in any form or manner. For example, a trench may be formed in the second dielectric layer 24 to allow the detected object 28 to be placed therein (not shown).

In accordance with some embodiments of the invention, the above-mentioned light guide element may be fabricated by the following method. For example, first, a patterned photoresist layer (not shown) is formed on the first dielectric layer 16, exposing the area where the trench 20 is defined later. Next, the first dielectric layer 16 is etched to an appropriate depth in the first dielectric layer 16 (i.e. does not extend past the first metal layer 30) using the patterned photoresist layer as a mask to form the trench 20 in the first dielectric layer 16. The filling material 22 is then filled in the trench 20. The fabrication of the above-mentioned light guide element is completed.

In accordance with some embodiments of the invention, the photoelectric conversion units 14 may be a photodiode (PD) or a sensing element. The sensing element may be composed of, for example, a photodiode, a transfer gate, a reset gate, a source-follow gate and a row-select gate.

In accordance with some embodiments of the invention, the first dielectric layer 16 may be an oxide layer.

In accordance with some embodiments of the invention, the filling material 22 may be a material with a refractive index higher than 1.4.

In accordance with some embodiments of the invention, the filling material 22 may be a material with a refractive index of 1.8-2.2, or a material which allows light with specific wavelengths to pass through, or a material which blocks light with specific wavelengths.

In accordance with some embodiments of the invention, the second dielectric layer 24 may be a silicon nitride layer or a tantalum oxide layer.

In accordance with some embodiments of the invention, the detected object 28 may be a biomolecule, such as DNA.

In this embodiment, the light emitted from the light source 26 is conducted to the photoelectric conversion units 14 through the light guide element formed by the trench 20.

In accordance with some embodiments of the invention, the excitation light emitted from the detected object 28 after being irradiated by the detection light source 29 may also be conducted to the photoelectric conversion units 14 through the light guide element formed by the trench 20, to detect or determine the characteristics of the detected object 28.

In this embodiment, if the trench 20 is filled with the high-refractive-index material 22, the light (signal) which enters the light guide element will be totally reflected in the trench 20 to achieve an improved condensing effect without formation of light penetration from both sides of the trench 20 to adjacent pixels, which effectively reduces the crosstalk phenomenon between adjacent pixels, and avoids color mixing between pixels.

Figure 2:
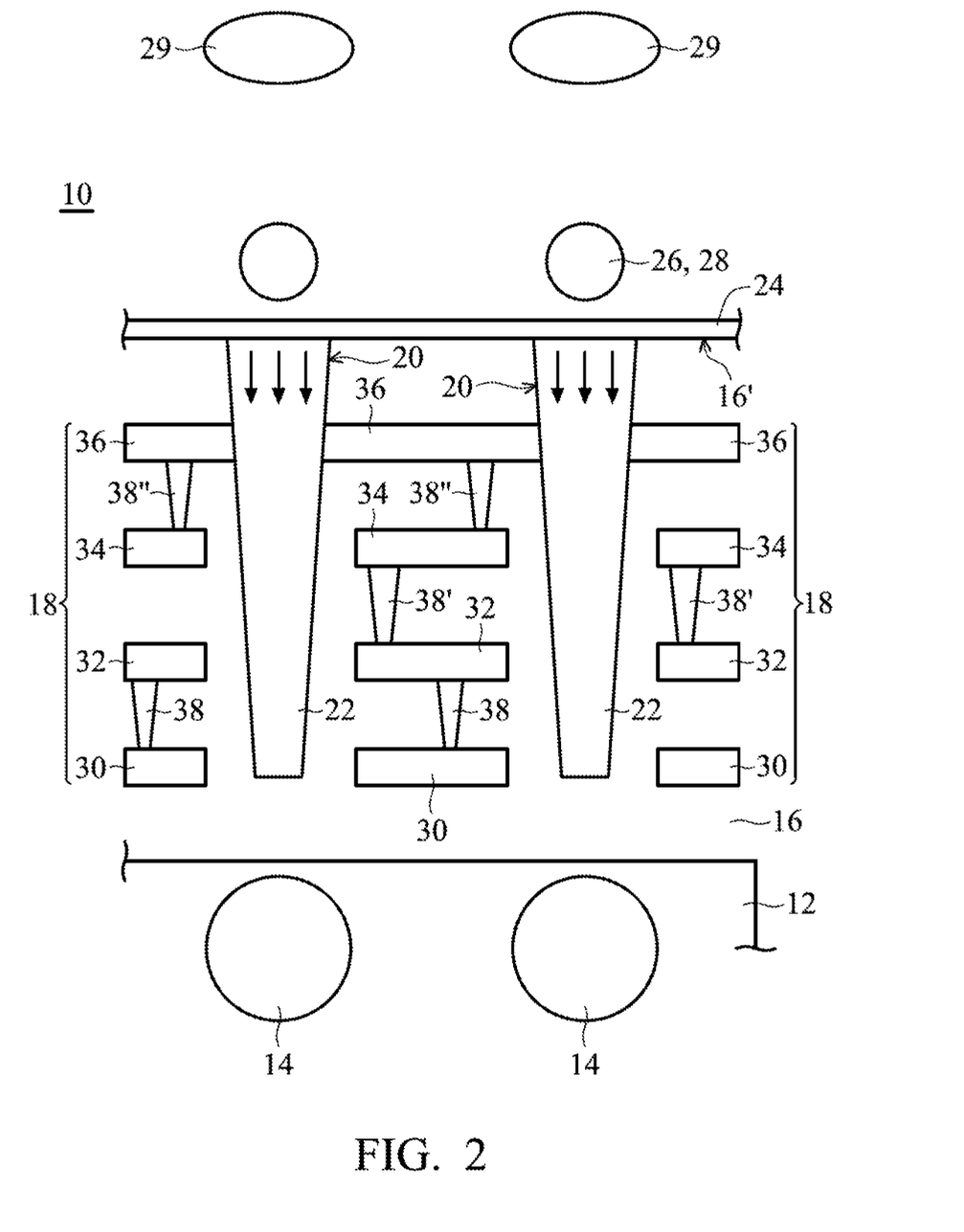
FIG. 2 is a cross-sectional view of an image sensor device in accordance with one embodiment of the invention.

Referring to FIG. 2, in accordance with one embodiment of the invention, an image sensor device 10 is disclosed. FIG. 2 is a cross-sectional view of the image sensor device 10 in this embodiment.

As shown in FIG. 2, the image sensor device 10 comprises a substrate 12, a plurality of photoelectric conversion units 14 for collecting image signals, a first dielectric layer 16, a plurality of metal layers 18, a trench 20, a filling material 22, a second dielectric layer 24 and a light source 26.

In this embodiment, the image sensor device 10 is a front side illumination (FSI) image sensor device.

In accordance with some embodiments of the invention, the image sensor device 10 may also comprise a detected object 28 and a detection light source 29.

As shown in FIG. 2, the photoelectric conversion units 14 are disposed in the substrate 12. The first dielectric layer 16 is disposed upon the substrate 12. The metal layers 18 are disposed in the first dielectric layer 16.

In this embodiment, the metal layers 18 comprise a first metal layer 30, a second metal layer 32, a third metal layer 34 and a top metal layer 36. The first metal layer 30 is adjacent to the substrate 12. The top metal layer 36 is adjacent to the top 16' of the first dielectric layer 16. Electrical connections are formed between individual metal layers by plugs (38, 38' and 38") in the metal layers 18. For example, an electrical connection is formed between the first metal layer 30 and the second metal layer 32 by a first plug 38. An electrical connection is formed between the second metal layer 32 and the third metal layer 34 by a second plug 38'. An electrical connection is formed between the third metal layer 34 and the top metal layer 36 by a third plug 38".

The trench 20 is disposed in the first dielectric layer 16 and located between the adjacent metal layers. For example, the trench 20 is located between the adjacent first metal layers 30, located between the adjacent second metal layers 32, located between the adjacent third metal layers 34, and located between the adjacent top metal layers 36. The trench 20 extends from the top 16' of the first dielectric layer 16 towards the substrate 12 to the first metal layer 30.

In this embodiment, the depth of the trench 20 extending towards the substrate 12 does not extend past the first metal layer 30. However, if the product is acceptable for the characteristics of high dark current, the trench 20 may also extend to the substrate 12.

Specifically, in this embodiment, the trench 20 substantially is in contact with the top metal layer 36. That is, no gap substantially exists between the trench 20 and the top metal layer 36.

In accordance with some embodiments of the invention, the trench 20 may also substantially be in contact with the other metal layers in the metal layers 18. That is, no gap substantially exists between the trench 20 and the other metal layers. For example, the trench 20 may substantially be in contact with the first metal layer 30, the trench 20 may substantially be in contact with the second metal layer 32, or the trench 20 may substantially be in contact with the third metal layer 34.

The filling material 22 filled in the trench 20 may comprise a high-refractive-index material, or a material which allows light with specific wavelengths to pass through, or a material which blocks light with specific wavelengths, to form a light guide element between the light source 26 or the detected object 28 and the photoelectric conversion units 14. The filling material 22 may also comprise other suitable materials, for example, a material that has a higher refractive index than that of the adjacent dielectric layer.

The second dielectric layer 24 is disposed upon the first dielectric layer 16. The light source 26 is disposed over the second dielectric layer 24.

In accordance with some embodiments of the invention, the detected object 28 may also be disposed over the second dielectric layer 24. The detected object 28 may be located over the second dielectric layer 24 in any form or manner. For example, a trench may be formed in the second dielectric layer 24 to allow the detected object 28 to be placed therein (not shown).

In accordance with some embodiments of the invention, the above-mentioned light guide element may be fabricated by the following method. For example, first, a patterned photoresist layer (not shown) is formed on the first dielectric layer 16, exposing the area where the trench 20 is defined later. Next, the first dielectric layer 16 and the top metal layer 36 are sequentially etched to an appropriate depth in the first dielectric layer 16 (i.e. does not extend past the first metal layer 30) using the patterned photoresist layer as a mask to form the trench 20 in the first dielectric layer 16. The filling material 22 is then filled in the trench 20. The fabrication of the above-mentioned light guide element is completed. Specifically, in the process of forming the metal layers 18 before the light guide element is formed, the metal layer 36 is not etched for the time being after the top metal layer 36 is formed. During the trench etching, the top metal layer 36 is simultaneously etched to complete a self-align fabrication between the metal layer and the trench.

In accordance with some embodiments of the invention, the photoelectric conversion units 14 may be a photodiode (PD) or a sensing element. The sensing element may be composed of, for example, a photodiode, a transfer gate, a reset gate, a source-follow gate and a row-select gate.

In accordance with some embodiments of the invention, the first dielectric layer 16 may be an oxide layer.

In accordance with some embodiments of the invention, the filling material 22 may be a material with a refractive index higher than 1.4.

In accordance with some embodiments of the invention, the filling material 22 may be a material with a refractive index of 1.8-2.2, or a material which allows light with specific wavelengths to pass through, or a material which blocks light with specific wavelengths.

In accordance with some embodiments of the invention, the second dielectric layer 24 may be a silicon nitride layer or a tantalum oxide layer.

In accordance with some embodiments of the invention, the detected object 28 may be a biomolecule, such as DNA.

In this embodiment, the light emitted from the light source 26 is conducted to the photoelectric conversion units 14 through the light guide element formed by the trench 20.

In accordance with some embodiments of the invention, the excitation light emitted from the detected object 28 after being irradiated by the detection light source 29 may also be conducted to the photoelectric conversion units 14 through the light guide element formed by the trench 20, to detect or determine the characteristics of the detected object 28.

In this embodiment, if the trench 20 is filled with the high-refractive-index material 22, the light (signal) which enters the light guide element will be totally reflected in the trench 20 to achieve an improved condensing effect without formation of light penetration from both sides of the trench 20 to adjacent pixels, which effectively reduces the crosstalk phenomenon between adjacent pixels, and avoids color mixing between pixels. In addition, since the trench 20 substantially is in contact with the top metal layer 36, merely the excitation light of the detected object enters the light guide element. The light (noise) emitted from the external light source is completely blocked by the top metal layer 36. Therefore, the light (noise) will not continue to penetrate downwards or towards the both sides of the light guide element, which effectively reduces the interference of the noise to the pixel or the neighboring pixels, and also improves the signal-to-noise ratio (SNR) of each pixel.

Figure 3:
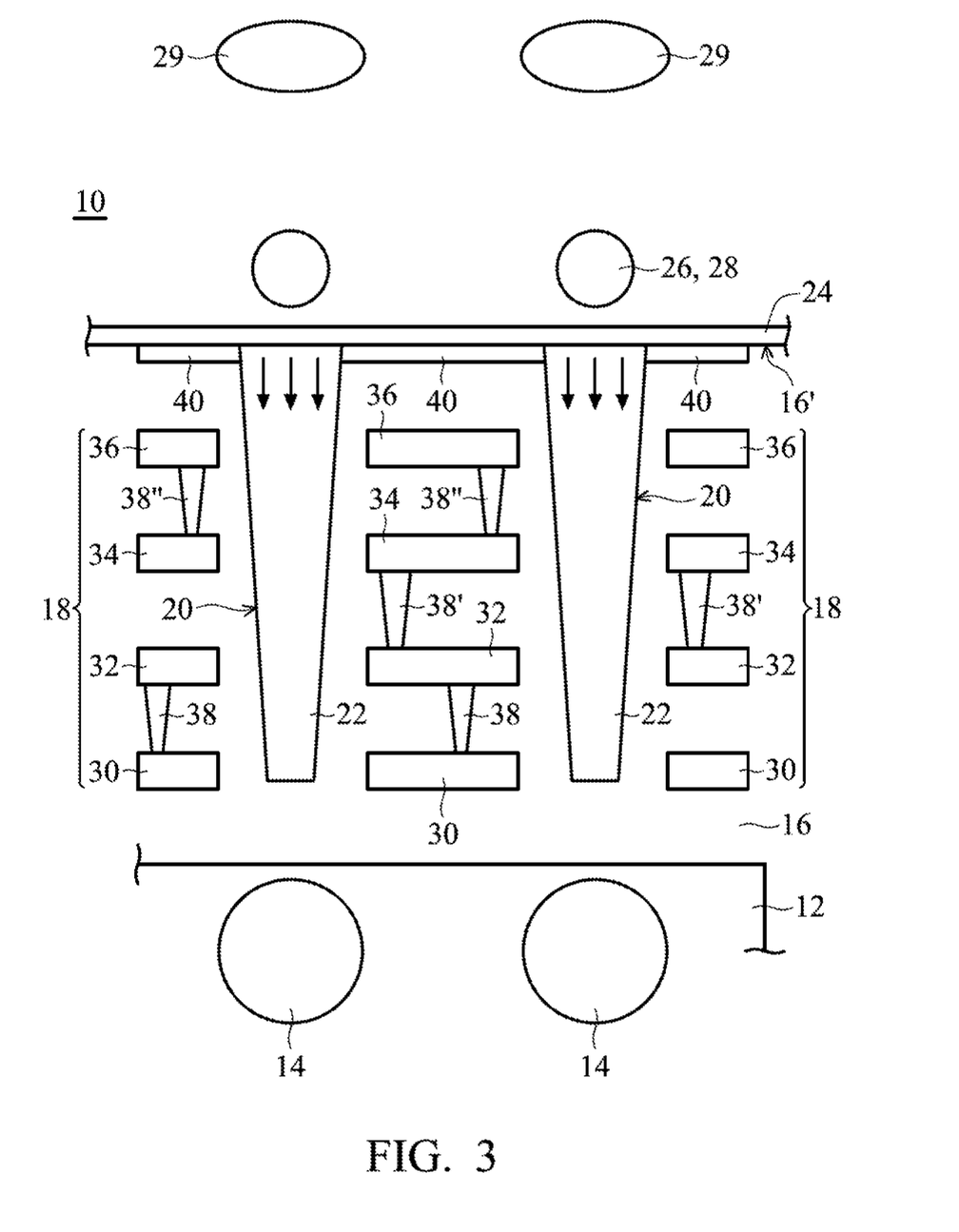
FIG. 3 is a cross-sectional view of an image sensor device in accordance with one embodiment of the invention.

Referring to FIG. 3, in accordance with one embodiment of the invention, an image sensor device 10 is disclosed. FIG. 3 is a cross-sectional view of the image sensor device 10 in this embodiment.

As shown in FIG. 3, the image sensor device 10 comprises a substrate 12, a plurality of photoelectric conversion units 14 for collecting image signals, a first dielectric layer 16, a plurality of metal layers 18, a trench 20, a filling material 22, a second dielectric layer 24 and a light source 26.

In this embodiment, the image sensor device 10 is a front side illumination (FSI) image sensor device.

In accordance with some embodiments of the invention, the image sensor device 10 may also comprise a detected object 28 and a detection light source 29.

As shown in FIG. 3, the photoelectric conversion units 14 are disposed in the substrate 12. The first dielectric layer 16 is disposed upon the substrate 12. The metal layers 18 are disposed in the first dielectric layer 16.

In this embodiment, the metal layers 18 comprise a first metal layer 30, a second metal layer 32, a third metal layer 34 and a top metal layer 36. The first metal layer 30 is adjacent to the substrate 12. The top metal layer 36 is adjacent to the top 16' of the first dielectric layer 16. Electrical connections are formed between individual metal layers by plugs (38, 38' and 38") in the metal layers 18. For example, an electrical connection is formed between the first metal layer 30 and the second metal layer 32 by a first plug 38. An electrical connection is formed between the second metal layer 32 and the third metal layer 34 by a second plug 38'. An electrical connection is formed between the third metal layer 34 and the top metal layer 36 by a third plug 38".

The trench 20 is disposed in the first dielectric layer 16 and located between the adjacent metal layers. For example, the trench 20 is located between the adjacent first metal layers 30, located between the adjacent second metal layers 32, located between the adjacent third metal layers 34, and located between the adjacent top metal layers 36. The trench 20 extends from the top 16' of the first dielectric layer 16 towards the substrate 12 to the first metal layer 30.

In this embodiment, the depth of the trench 20 extending towards the substrate 12 does not extend past the first metal layer 30. However, if the product is acceptable for the characteristics of high dark current, the trench 20 may also extend to the substrate 12.

Specifically, in this embodiment, the image sensor device 10 further comprises a light-shielding layer 40 disposed at the top 16' of the first dielectric layer 16.

In accordance with some embodiments of the invention, the light-shielding layer 40 may also be disposed at any appropriate position in the metal layers 18. For example, the light-shielding layer 40 may be disposed between the first metal layer 30 and the second metal layer 32, or disposed between the second metal layer 32 and the third metal layer 34, or disposed between the third metal layer 34 and the top metal layer 36.

In accordance with some embodiments of the invention, the light-shielding layer 40 may comprise metals such as aluminum, copper or tungsten, or related light-blocking materials or light-absorbing materials.

In accordance with some embodiments of the invention, an appropriate thickness of the light-shielding layer 40 may be defined according to different light-shielding requirements.

Specifically, in this embodiment, the trench 20 substantially is in contact with the light-shielding layer 40 which is disposed at the top 16' of the first dielectric layer 16. That is, no gap substantially exists between the trench 20 and the light-shielding layer 40.

In accordance with some embodiments of the invention, the trench 20 may also substantially be in contact with the light-shielding layer 40 which is disposed between the metal layers 18.

The filling material 22 filled in the trench 20 may comprise a high-refractive-index material, or a material which allows light with specific wavelengths to pass through, or a material which blocks light with specific wavelengths, to form a light guide element between the light source 26 or the detected object 28 and the photoelectric conversion units 14.

The filling material 22 may also comprise other suitable materials, for example, a material that has a higher refractive index than that of the adjacent dielectric layer.

The second dielectric layer 24 is disposed upon the first dielectric layer 16. The light source 26 is disposed over the second dielectric layer 24.

In accordance with some embodiments of the invention, the detected object 28 may also be disposed over the second dielectric layer 24. The detected object 28 may be located over the second dielectric layer 24 in any form or manner. For example, a trench may be formed in the second dielectric layer 24 to allow the detected object 28 to be placed therein (not shown).

In accordance with some embodiments of the invention, the above-mentioned light guide element may be fabricated by the following method. For example, first, a patterned photoresist layer (not shown) is formed on the light-shielding layer 40 and the first dielectric layer 16, exposing the area where the trench 20 is defined later. Next, the light-shielding layer 40 and the first dielectric layer 16 are sequentially etched to an appropriate depth in the first dielectric layer 16 (i.e. does not extend past the first metal layer 30) using the patterned photoresist layer as a mask to form the trench 20 in the first dielectric layer 16. The filling material 22 is then filled in the trench 20. The fabrication of the above-mentioned light guide element is completed. Specifically, in the process of forming the light-shielding layer 40 before the light guide element is formed, the light-shielding layer 40 is not etched for the time being after the light-shielding layer 40 is formed. During the trench etching, the light-shielding layer 40 is simultaneously etched to complete a self-align fabrication between the light-shielding layer and the trench.

In accordance with some embodiments of the invention, the photoelectric conversion units 14 may be a photodiode (PD) or a sensing element. The sensing element may be composed of, for example, a photodiode, a transfer gate, a reset gate, a source-follow gate and a row-select gate.

In accordance with some embodiments of the invention, the first dielectric layer 16 may be an oxide layer.

In accordance with some embodiments of the invention, the filling material 22 may be a material with a refractive index higher than 1.4.

In accordance with some embodiments of the invention, the filling material 22 may be a material with a refractive index of 1.8-2.2, or a material which allows light with specific wavelengths to pass through, or a material which blocks light with specific wavelengths.

In accordance with some embodiments of the invention, the second dielectric layer 24 may be a silicon nitride layer or a tantalum oxide layer.

In accordance with some embodiments of the invention, the detected object 28 may be a biomolecule, such as DNA.

In this embodiment, the light emitted from the light source 26 is conducted to the photoelectric conversion units 14 through the light guide element formed by the trench 20.

In accordance with some embodiments of the invention, the excitation light emitted from the detected object 28 after being irradiated by the detection light source 29 may also be conducted to the photoelectric conversion units 14 through the light guide element formed by the trench 20, to detect or determine the characteristics of the detected object 28.

In this embodiment, if the trench 20 is filled with the high-refractive-index material 22, the light (signal) which enters the light guide element will be totally reflected in the trench 20 to achieve an improved condensing effect without formation of light penetration from both sides of the trench 20 to adjacent pixels, which effectively reduces the crosstalk phenomenon between adjacent pixels, and avoids color mixing between pixels. In addition, since the trench 20 substantially is in contact with the top light-shielding layer 40, merely the excitation light of the detected object enters the light guide element. The light (noise) emitted from the external light source is completely blocked by the light-shielding layer 40. Therefore, the light (noise) will not continue to penetrate downwards or towards the both sides of the light guide element, which effectively reduces the interference of the noise to the pixel or the neighboring pixels, and also improves the signal-to-noise ratio (SNR) of each pixel.

In the invention, the light-shielding layer 40 may alternatively be disposed on the top 16' of the first dielectric layer 16 or disposed in any appropriate position in the metal layers 18 so as not to affect the original process of the metal layers and the related circuit operation.

Figure 4:
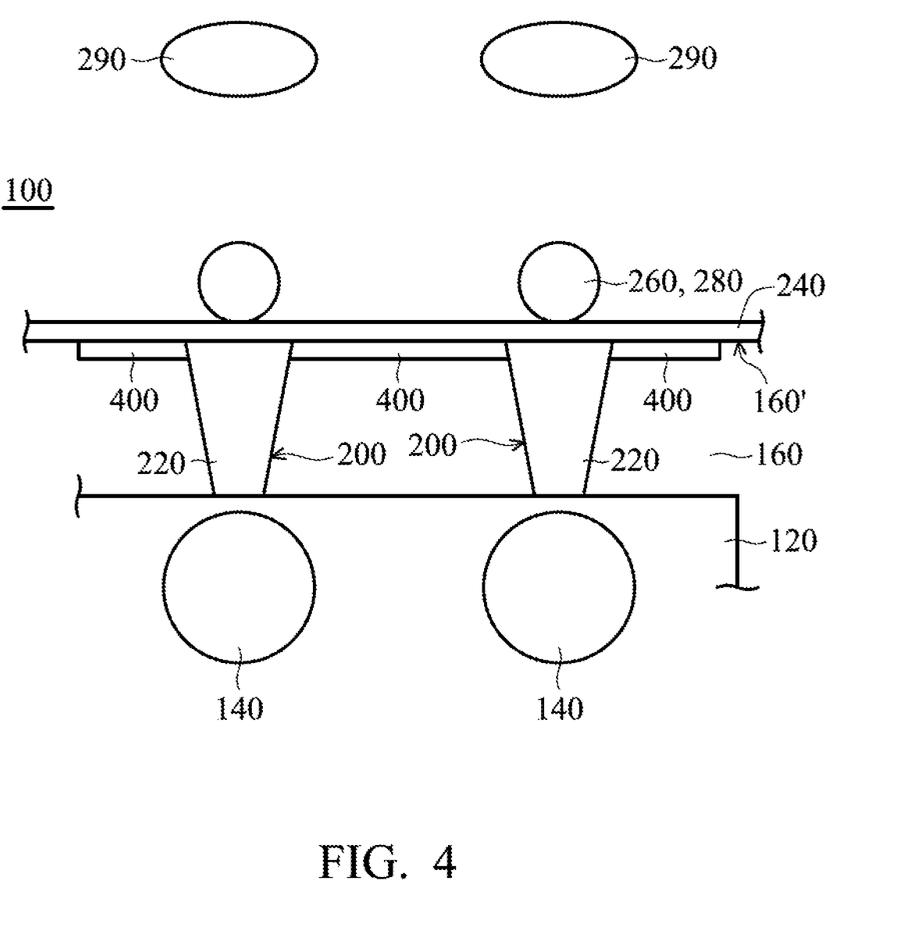
FIG. 4 is a cross-sectional view of an image sensor device in accordance with one embodiment of the invention.

Referring to FIG. 4, in accordance with one embodiment of the invention, an image sensor device 100 is disclosed. FIG. 4 is a cross-sectional view of the image sensor device 100 in this embodiment.

As shown in FIG. 4, the image sensor device 100 comprises a substrate 120, a plurality of photoelectric conversion units 140 for collecting image signals, a first dielectric layer 160, a light-shielding layer 400, a trench 200, a filling material 220, a second dielectric layer 240 and a light source 260.

In this embodiment, the image sensor device 100 is a back side illumination (BSI) image sensor device.

In accordance with some embodiments of the invention, the image sensor device 100 may also comprise a detected object 280 and a detection light source 290.

As shown in FIG. 4, the photoelectric conversion units 140 are disposed in the substrate 120. The first dielectric layer 160 is disposed upon the substrate 120. The light-shielding layer 400 is disposed at the top 160' of the first dielectric layer 160.

Specifically, in this embodiment, the trench 200 is disposed in the first dielectric layer 160 and extends from the top 160' of the first dielectric layer 160 to the substrate 120 and substantially is in contact with the light-shielding layer 400. That is, no gap substantially exists between the trench 200 and the light-shielding layer 400.

The filling material 220 filled in the trench 200 may comprise a high-refractive-index material, or a material which allows light with specific wavelengths to pass through, or a material which blocks light with specific wavelengths, to form a light guide element between the light source 260 or the detected object 280 and the photoelectric conversion units 140. The filling material 220 may also comprise other suitable materials, for example, a material that has a higher refractive index than that of the adjacent dielectric layer.

The second dielectric layer 240 is disposed upon the first dielectric layer 160. The light source 260 is disposed over the second dielectric layer 240.

In accordance with some embodiments of the invention, the detected object 280 may also be disposed over the second dielectric layer 240. The detected object 280 may be located over the second dielectric layer 240 in any form or manner. For example, a trench may be formed in the second dielectric layer 240 to allow the detected object 280 to be placed therein (not shown).

In accordance with some embodiments of the invention, the above-mentioned light guide element may be fabricated by the following method. For example, first, a patterned photoresist layer (not shown) is formed on the light-shielding layer 400 and the first dielectric layer 160, exposing the area where the trench 200 is defined later. Next, the light-shielding layer 400 and the first dielectric layer 160 are sequentially etched to an appropriate depth in the first dielectric layer 160 (i.e. etching to the substrate 120) using the patterned photoresist layer as a mask to form the trench 200 in the first dielectric layer 160. The filling material 220 is then filled in the trench 200. The fabrication of the above-mentioned light guide element is completed. Specifically, in the process of forming the light-shielding layer 400 before the light guide element is formed, the light-shielding layer 400 is not etched for the time being after the light-shielding layer 400 is formed. During the trench etching, the light-shielding layer 400 is simultaneously etched to complete a self-align fabrication between the light-shielding layer and the trench.

In accordance with some embodiments of the invention, the photoelectric conversion units 140 may be a photodiode (PD) or a sensing element. The sensing element may be composed of, for example, a photodiode, a transfer gate, a reset gate, a source-follow gate and a row-select gate.

In accordance with some embodiments of the invention, the first dielectric layer 160 may be an oxide layer.

In accordance with some embodiments of the invention, the light-shielding layer 400 may comprise metals such as aluminum, copper or tungsten, or related light-blocking materials or light-absorbing materials.

In accordance with some embodiments of the invention, an appropriate thickness of the light-shielding layer 400 may be defined according to different light-shielding requirements.

In accordance with some embodiments of the invention, the filling material 220 may be a material with a refractive index higher than 1.4.

In accordance with some embodiments of the invention, the filling material 220 may be a material with a refractive index of 1.8-2.2, or a material which allows light with specific wavelengths to pass through, or a material which blocks light with specific wavelengths.

In accordance with some embodiments of the invention, the second dielectric layer 240 may be a silicon nitride layer or a tantalum oxide layer.

In accordance with some embodiments of the invention, the detected object 280 may be a biomolecule, such as DNA.

In this embodiment, the light emitted from the light source 260 is conducted to the photoelectric conversion units 140 through the light guide element formed by the trench 200.

In accordance with some embodiments of the invention, the excitation light emitted from the detected object 280 after being irradiated by the detection light source 290 may also be conducted to the photoelectric conversion units 140 through the light guide element formed by the trench 200, to detect or determine the characteristics of the detected object 280.

In this embodiment, if the trench 200 is filled with the high-refractive-index material 220, the light (signal) which enters the light guide element will be totally reflected in the trench 200 to achieve an improved condensing effect without formation of light penetration from both sides of the trench 200 to adjacent pixels, which effectively reduces the cross-talk phenomenon between adjacent pixels, and avoids color mixing between pixels. In addition, since the trench 200 substantially is in contact with the light-shielding layer 400, merely the excitation light of the detected object enters the light guide element. The light (noise) emitted from the external light source is completely blocked by the light-shielding layer 400. Therefore, the light (noise) will not continue to penetrate downwards or towards the both sides of the light guide element, which effectively reduces the interference of the noise to the pixel or the neighboring pixels, and also improves the signal-to-noise ratio (SNR) of each pixel.

It will be apparent to those skilled in the art that various modifications and variations can be made to the disclosed embodiments. It is intended that the specification and examples be considered as exemplary only, with the true scope of the invention being indicated by the following claims and their equivalents.

What is claimed is:

1. An image sensor device, comprising:
   a substrate;
   a plurality of photoelectric conversion units for collecting image signals disposed in the substrate;
   a first dielectric layer disposed upon the substrate;
   a plurality of metal layers disposed in the first dielectric layer, wherein each metal layer adjacent to the substrate is defined as a first metal layer, and each metal layer adjacent to the top of the first dielectric layer is defined as a top metal layer;
   a trench disposed in the first dielectric layer and located between adjacent metal layers, extending from the top of the first dielectric layer towards the substrate to the first metal layer;
   a filling material filled in the trench;
   a second dielectric layer disposed upon the first dielectric layer and the trench, and directly contacting with the first dielectric layer and the trench; and
   a light source or a detected object disposed over the second dielectric layer.

2. The image sensor device as claimed in claim 1, wherein the first dielectric layer is an oxide layer.

3. The image sensor device as claimed in claim 1, wherein the filling material is a material which has a refractive index higher than 1.4.

4. The image sensor device as claimed in claim 1, wherein the filling material comprises a material which has a refractive index of 1.8-2.2, or a material which allows light with specific wavelengths to pass through, or a material which blocks light with specific wavelengths.

5. The image sensor device as claimed in claim 1, wherein the second dielectric layer is a silicon nitride layer or a tantalum oxide layer.

6. The image sensor device as claimed in claim 1, wherein the trench is in contact with the top metal layer, and there is no gap therebetween.

7. The image sensor device as claimed in claim 1, further comprising a light-shielding layer disposed at the top of the first dielectric layer.

8. The image sensor device as claimed in claim 7, wherein the light-shielding layer comprises metals, light-blocking materials, or light-absorbing materials.

9. The image sensor device as claimed in claim 7, wherein the trench is in contact with the light-shielding layer, and there is no gap therebetween.

10. The image sensor device as claimed in claim 1, wherein the detected object is biomolecules.

11. An image sensor device, comprising:
    a substrate;
    a plurality of photoelectric conversion units for collecting image signals disposed in the substrate;
    a first dielectric layer disposed upon the substrate;
    a light-shielding layer disposed at the top of the first dielectric layer;
    a trench disposed in the first dielectric layer, extending from the top of the first dielectric layer to the substrate and contacting the light-shielding layer;
    a filling material filled in the trench;
    a second dielectric layer disposed upon the first dielectric layer and the trench, and directly contacting with the first dielectric layer and the trench; and
    a light source or a detected object disposed over the second dielectric layer.

12. The image sensor device as claimed in claim 11, wherein the first dielectric layer is an oxide layer.

13. The image sensor device as claimed in claim 11, wherein the light-shielding layer comprises metals, light-blocking materials, or light-absorbing materials.

14. The image sensor device as claimed in claim 11, wherein the filling material is a material which has a refractive index higher than 1.4.

15. The image sensor device as claimed in claim 11, wherein the filling material comprises a material which has a refractive index of 1.8-2.2, or a material which allows light with specific wavelengths to pass through, or a material which blocks light with specific wavelengths.

16. The image sensor device as claimed in claim 11, wherein the second dielectric layer is a silicon nitride layer or a tantalum oxide layer.

17. The image sensor device as claimed in claim 11, wherein the detected object is biomolecules.

* * * * *